(12) United States Patent
Shelton et al.

(10) Patent No.: US 10,029,090 B2
(45) Date of Patent: Jul. 24, 2018

(54) MULTI-BRANCH STIMULATION ELECTRODE FOR SUBCUTANEOUS FIELD STIMULATION

(71) Applicant: ALFRED E. MANN FOUNDATION FOR SCIENTIFIC RESEARCH, Santa Clarita, CA (US)

(72) Inventors: Brian M. Shelton, Altadena, CA (US); Morten Hansen, Valencia, CA (US)

(73) Assignee: ALFRED E. MANN FOUNDATION FOR SCIENTIFIC RESEARCH, Santa Clarita, CA (US)

( * ) Notice: Subject to any disclaimer, the term of this patent is extended or adjusted under 35 U.S.C. 154(b) by 0 days.

(21) Appl. No.: 15/232,632

(22) Filed: Aug. 9, 2016

(65) Prior Publication Data

US 2016/0346532 A1 Dec. 1, 2016

Related U.S. Application Data

(62) Division of application No. 14/270,075, filed on May 5, 2014, now Pat. No. 9,433,779.

(Continued)

(51) Int. Cl.
*A61N 1/05* (2006.01)
*A61N 1/375* (2006.01)
*A61N 1/36* (2006.01)

(52) U.S. Cl.
CPC ......... *A61N 1/0551* (2013.01); *A61N 1/0504* (2013.01); *A61N 1/36125* (2013.01); *A61N 1/3752* (2013.01)

(58) Field of Classification Search
CPC .. A61N 1/0526–1/0539; A61N 1/0551; A61N 1/0558; A61N 2001/0578
See application file for complete search history.

(56) References Cited

U.S. PATENT DOCUMENTS 3,646,940 A 3/1972 Timm et al.
3,942,535 A 3/1976 Schulman et al.
(Continued)

FOREIGN PATENT DOCUMENTS

DE 102010006837 A1 8/2011
EP 1680182 7/2006
(Continued)

OTHER PUBLICATIONS

Boiocchi, S., et al., "Self-calibration in high speed current steering CMOS D/A converters", Advanced A-D and D-A Conversion Techniques and Their Applications, 1994, Second International Conference on Cambridge, UK, London, UK, IEE, UK, Jan. 1, 1994 (Jan. 1, 1994), pp. 148-152.
(Continued)

*Primary Examiner* — Kennedy Schaetzle
(74) *Attorney, Agent, or Firm* — Kilpatrick Townsend & Stockton LLP

(57) ABSTRACT

A multi-branch stimulation electrode is disclosed herein. The multi-branch stimulation electrode can include a plurality of branches that extend from a hub. The branches can each include one or several stimulation contacts that can deliver an electrical current to tissue contacting the stimulation contacts. The stimulation contacts can be electrically connected with the lead. The lead can extend from the hub and can be connected with the pulse generator. The branches can include features to facilitate implantation including, for example, one or several removable stiffening elements.

13 Claims, 8 Drawing Sheets

Related U.S. Application Data

(60) Provisional application No. 61/819,441, filed on May 3, 2013.

(56) References Cited

U.S. PATENT DOCUMENTS

| | | |
|---|---|---|
| 4,019,518 A | 4/1977 | Maurer et al. |
| 4,044,774 A | 8/1977 | Corbin et al. |
| 4,082,097 A | 4/1978 | Mann et al. |
| 4,112,952 A * | 9/1978 | Thomas .............. A61N 1/0587 607/128 |
| 4,340,062 A | 7/1982 | Thompson et al. |
| 4,468,723 A | 8/1984 | Hughes |
| 4,558,702 A | 12/1985 | Barreras et al. |
| 4,673,867 A | 6/1987 | Davis |
| 4,744,371 A | 5/1988 | Harris |
| 5,143,089 A | 9/1992 | Alt |
| 5,282,845 A * | 2/1994 | Bush .................. A61N 1/0587 607/127 |
| 5,690,693 A | 11/1997 | Wang et al. |
| 5,702,428 A | 12/1997 | Tippey et al. |
| 5,702,431 A | 12/1997 | Wang et al. |
| 5,735,887 A | 4/1998 | Barreras, Sr. et al. |
| 5,741,316 A | 4/1998 | Chen et al. |
| 5,876,423 A | 3/1999 | Braun |
| 5,877,472 A | 3/1999 | Campbell et al. |
| 6,027,456 A | 2/2000 | Feler et al. |
| 6,035,237 A | 3/2000 | Schulman et al. |
| 6,055,456 A | 4/2000 | Gerber |
| 6,057,513 A | 5/2000 | Ushikoshi et al. |
| 6,067,474 A | 5/2000 | Schulman et al. |
| 6,076,017 A | 6/2000 | Taylor et al. |
| 6,164,284 A | 12/2000 | Schulman et al. |
| 6,172,556 B1 | 1/2001 | Prentice |
| 6,178,353 B1 | 1/2001 | Griffith et al. |
| 6,185,452 B1 | 2/2001 | Schulman et al. |
| 6,191,365 B1 | 2/2001 | Avellanet |
| 6,208,894 B1 | 3/2001 | Schulman et al. |
| 6,212,431 B1 | 4/2001 | Hahn et al. |
| 6,221,513 B1 | 4/2001 | Lasater |
| 6,246,911 B1 | 6/2001 | Seligman |
| 6,249,703 B1 | 6/2001 | Stanton et al. |
| 6,265,789 B1 | 7/2001 | Honda et al. |
| 6,306,100 B1 | 10/2001 | Prass |
| 6,313,779 B1 | 11/2001 | Leung et al. |
| 6,315,721 B2 | 11/2001 | Schulman et al. |
| 6,354,991 B1 | 3/2002 | Gross et al. |
| 6,360,750 B1 | 3/2002 | Gerber et al. |
| 6,393,325 B1 | 5/2002 | Mann et al. |
| 6,427,086 B1 | 7/2002 | Fischell et al. |
| 6,438,423 B1 | 8/2002 | Rezai et al. |
| 6,442,434 B1 | 8/2002 | Zarinetchi et al. |
| 6,466,817 B1 | 10/2002 | Kaula et al. |
| 6,505,075 B1 | 1/2003 | Weiner |
| 6,516,227 B1 | 2/2003 | Meadows et al. |
| 6,521,350 B2 | 2/2003 | Fey et al. |
| 6,564,807 B1 | 5/2003 | Schulman et al. |
| 6,584,355 B2 | 6/2003 | Stessman |
| 6,600,954 B2 | 7/2003 | Cohen et al. |
| 6,609,031 B1 | 8/2003 | Law et al. |
| 6,609,032 B1 | 8/2003 | Woods et al. |
| 6,652,449 B1 | 11/2003 | Gross |
| 6,662,051 B1 | 12/2003 | Eraker et al. |
| 6,721,603 B2 | 4/2004 | Zabara et al. |
| 6,735,474 B1 | 5/2004 | Loeb et al. |
| 6,745,077 B1 | 6/2004 | Griffith et al. |
| 6,809,701 B2 | 10/2004 | Amundson et al. |
| 6,836,684 B1 | 12/2004 | Rijkhoff et al. |
| 6,847,849 B2 | 1/2005 | Mama et al. |
| 6,864,755 B2 | 3/2005 | Moore |
| 6,892,098 B2 | 5/2005 | Ayal et al. |
| 6,895,280 B2 | 5/2005 | Meadows et al. |
| 6,896,651 B2 | 5/2005 | Gross et al. |
| 6,901,287 B2 | 5/2005 | Davis et al. |
| 6,941,171 B2 | 9/2005 | Mann et al. |
| 6,971,393 B1 | 12/2005 | Mama et al. |
| 6,986,453 B2 | 1/2006 | Jiang et al. |
| 6,989,200 B2 | 1/2006 | Byers et al. |
| 6,990,376 B2 | 1/2006 | Tanagho et al. |
| 6,999,819 B2 | 2/2006 | Swoyer et al. |
| 7,051,419 B2 | 5/2006 | Schrom et al. |
| 7,054,689 B1 | 5/2006 | Whitehurst et al. |
| 7,069,081 B2 | 6/2006 | Biggs et al. |
| 7,114,502 B2 | 10/2006 | Schulman et al. |
| 7,127,298 B1 | 10/2006 | He et al. |
| 7,142,925 B1 | 11/2006 | Bhadra et al. |
| 7,146,219 B2 | 12/2006 | Sieracki et al. |
| 7,151,914 B2 | 12/2006 | Brewer |
| 7,167,749 B2 | 1/2007 | Biggs et al. |
| 7,177,690 B2 | 2/2007 | Woods et al. |
| 7,177,698 B2 | 2/2007 | Klosterman et al. |
| 7,181,286 B2 | 2/2007 | Sieracki et al. |
| 7,187,978 B2 | 3/2007 | Malek et al. |
| 7,191,005 B2 | 3/2007 | Stessman |
| 7,212,110 B1 | 5/2007 | Martin et al. |
| 7,225,032 B2 | 5/2007 | Schmeling et al. |
| 7,231,254 B2 | 6/2007 | Dilorenzo |
| 7,234,853 B2 | 6/2007 | Givoletti |
| 7,245,972 B2 | 7/2007 | Davis |
| 7,286,880 B2 | 10/2007 | Olson et al. |
| 7,305,268 B2 | 12/2007 | Gliner et al. |
| 7,317,948 B1 | 1/2008 | King et al. |
| 7,324,852 B2 | 1/2008 | Barolat et al. |
| 7,324,853 B2 | 1/2008 | Ayal et al. |
| 7,328,068 B2 | 2/2008 | Spinelli et al. |
| 7,330,764 B2 | 2/2008 | Swoyer et al. |
| 7,331,499 B2 | 2/2008 | Jiang et al. |
| 7,359,751 B1 | 4/2008 | Erickson et al. |
| 7,369,894 B2 | 5/2008 | Gerber |
| 7,386,348 B2 | 6/2008 | North et al. |
| 7,387,603 B2 | 6/2008 | Gross et al. |
| 7,396,265 B2 | 7/2008 | Darley et al. |
| 7,415,308 B2 | 8/2008 | Gerber et al. |
| 7,444,181 B2 | 10/2008 | Shi et al. |
| 7,450,991 B2 | 11/2008 | Smith et al. |
| 7,460,911 B2 | 12/2008 | Cosendai et al. |
| 7,463,928 B2 | 12/2008 | Lee et al. |
| 7,470,236 B1 | 12/2008 | Kelleher et al. |
| 7,483,752 B2 | 1/2009 | Von Arx et al. |
| 7,496,404 B2 | 2/2009 | Meadows et al. |
| 7,513,257 B2 | 4/2009 | Schulman et al. |
| 7,515,967 B2 | 4/2009 | Phillips et al. |
| 7,532,936 B2 | 5/2009 | Erickson et al. |
| 7,539,538 B2 | 5/2009 | Parramon et al. |
| 7,551,960 B2 | 6/2009 | Forsberg et al. |
| 7,555,346 B1 | 6/2009 | Woods et al. |
| 7,565,203 B2 | 7/2009 | Greenberg et al. |
| 7,578,819 B2 | 8/2009 | Bleich et al. |
| 7,580,752 B2 | 8/2009 | Gerber et al. |
| 7,582,053 B2 | 9/2009 | Gross et al. |
| 7,617,002 B2 | 11/2009 | Goetz |
| 7,640,059 B2 | 12/2009 | Forsberg et al. |
| 7,643,880 B2 | 1/2010 | Tanagho et al. |
| 7,706,889 B2 | 4/2010 | Gerber et al. |
| 7,720,547 B2 | 5/2010 | Denker et al. |
| 7,725,191 B2 | 5/2010 | Greenberg et al. |
| 7,734,355 B2 | 6/2010 | Cohen et al. |
| 7,738,963 B2 | 6/2010 | Hickman et al. |
| 7,738,965 B2 | 6/2010 | Phillips et al. |
| 7,747,330 B2 | 6/2010 | Nolan et al. |
| 7,771,838 B1 | 8/2010 | He et al. |
| 7,774,069 B2 | 8/2010 | Olson et al. |
| 7,801,619 B2 | 9/2010 | Gerber et al. |
| 7,813,803 B2 | 10/2010 | Heruth et al. |
| 7,813,809 B2 | 10/2010 | Strother et al. |
| 7,826,901 B2 | 11/2010 | Lee et al. |
| 7,848,818 B2 | 12/2010 | Barolat et al. |
| 7,904,167 B2 | 3/2011 | Klosterman et al. |
| 7,912,555 B2 | 3/2011 | Swoyer et al. |
| 7,925,357 B2 | 4/2011 | Phillips et al. |
| 7,932,696 B2 | 4/2011 | Peterson |
| 7,933,656 B2 | 4/2011 | Sieracki et al. |
| 7,935,051 B2 | 5/2011 | Miles et al. |
| 7,937,158 B2 | 5/2011 | Erickson et al. |

(56) References Cited

U.S. PATENT DOCUMENTS

| | | |
|---|---|---|
| 7,952,349 B2 | 5/2011 | Huang et al. |
| 7,957,818 B2 | 6/2011 | Swoyer |
| 7,979,119 B2 | 7/2011 | Kothandaraman et al. |
| 7,979,126 B2 | 7/2011 | Payne et al. |
| 7,988,507 B2 | 8/2011 | Darley et al. |
| 8,000,782 B2 | 8/2011 | Gharib et al. |
| 8,000,805 B2 | 8/2011 | Swoyer et al. |
| 8,005,535 B2 | 8/2011 | Gharib et al. |
| 8,005,549 B2 | 8/2011 | Boser et al. |
| 8,005,550 B2 | 8/2011 | Boser et al. |
| 8,019,423 B2 | 9/2011 | Passover |
| 8,024,047 B2 | 9/2011 | Olson et al. |
| 8,036,756 B2 | 10/2011 | Swoyer et al. |
| 8,044,635 B2 | 10/2011 | Peterson |
| 8,050,769 B2 | 11/2011 | Gharib et al. |
| 8,055,337 B2 | 11/2011 | Moffitt et al. |
| 8,068,912 B2 | 11/2011 | Kaula et al. |
| 8,083,663 B2 | 12/2011 | Gross |
| 8,103,360 B2 | 1/2012 | Foster |
| 8,116,862 B2 | 2/2012 | Stevenson et al. |
| 8,121,701 B2 | 2/2012 | Woods et al. |
| 8,129,942 B2 | 3/2012 | Park et al. |
| 8,131,358 B2 | 3/2012 | Moffitt et al. |
| 8,140,168 B2 | 3/2012 | Olson et al. |
| 8,145,324 B1 | 3/2012 | Stevenson et al. |
| 8,150,530 B2 | 4/2012 | Wesselink |
| 8,175,717 B2 | 5/2012 | Hailer et al. |
| 8,180,451 B2 | 5/2012 | Hickman et al. |
| 8,180,452 B2 | 5/2012 | Shaquer |
| 8,180,461 B2 | 5/2012 | Mama et al. |
| 8,214,042 B2 | 7/2012 | Ozawa et al. |
| 8,214,048 B1 | 7/2012 | Whitehurst et al. |
| 8,214,051 B2 | 7/2012 | Sieracki et al. |
| 8,219,196 B2 | 7/2012 | Torgerson |
| 8,219,202 B2 | 7/2012 | Giftakis et al. |
| 8,233,990 B2 | 7/2012 | Goetz |
| 8,255,057 B2 | 8/2012 | Fang et al. |
| 8,311,636 B2 | 11/2012 | Gerber et al. |
| 8,314,594 B2 | 11/2012 | Scott et al. |
| 8,332,040 B1 | 12/2012 | Winstrom |
| 8,340,786 B2 | 12/2012 | Gross et al. |
| 8,362,742 B2 | 1/2013 | Kallmyer |
| 8,369,943 B2 | 2/2013 | Shuros et al. |
| 8,386,048 B2 | 2/2013 | McClure et al. |
| 8,417,346 B2 | 4/2013 | Giftakis et al. |
| 8,423,146 B2 | 4/2013 | Giftakis et al. |
| 8,447,402 B1 | 5/2013 | Jiang et al. |
| 8,447,408 B2 | 5/2013 | North et al. |
| 8,457,756 B2 | 6/2013 | Rahman |
| 8,457,758 B2 | 6/2013 | Olson et al. |
| 8,480,437 B2 | 7/2013 | Dilmaghanian et al. |
| 8,494,625 B2 | 7/2013 | Hargrove |
| 8,515,545 B2 | 8/2013 | Trier |
| 8,538,530 B1 | 9/2013 | Orinski |
| 8,543,223 B2 | 9/2013 | Sage et al. |
| 8,549,015 B2 | 10/2013 | Barolat |
| 8,554,322 B2 | 10/2013 | Olson et al. |
| 8,555,894 B2 | 10/2013 | Schulman et al. |
| 8,562,539 B2 | 10/2013 | Marino |
| 8,571,677 B2 | 10/2013 | Torgerson et al. |
| 8,577,474 B2 | 11/2013 | Rahman et al. |
| 8,588,917 B2 | 11/2013 | Whitehurst et al. |
| 8,626,314 B2 | 1/2014 | Swoyer et al. |
| 8,644,933 B2 | 2/2014 | Ozawa et al. |
| 8,655,451 B2 | 2/2014 | Klosterman et al. |
| 8,700,175 B2 | 4/2014 | Fell |
| 8,725,269 B2 | 5/2014 | Nolan et al. |
| 8,738,141 B2 | 5/2014 | Smith et al. |
| 8,738,148 B2 | 5/2014 | Olson et al. |
| 8,750,985 B2 | 6/2014 | Parramon et al. |
| 8,761,897 B2 | 6/2014 | Kaula et al. |
| 8,768,452 B2 | 7/2014 | Gerber |
| 8,774,912 B2 | 7/2014 | Gerber |
| 8,954,148 B2 | 2/2015 | Labbe et al. |
| 8,989,861 B2 | 3/2015 | Su et al. |
| 9,089,712 B2 | 7/2015 | Joshi et al. |
| 9,108,063 B2 | 8/2015 | Olson et al. |
| 2002/0116042 A1 | 8/2002 | Boling |
| 2003/0078633 A1 | 4/2003 | Firlik et al. |
| 2004/0106963 A1 | 6/2004 | Tsukamoto et al. |
| 2005/0104577 A1 | 5/2005 | Matei et al. |
| 2006/0016452 A1 | 1/2006 | Goetz et al. |
| 2006/0050539 A1 | 3/2006 | Yang et al. |
| 2006/0142822 A1 | 6/2006 | Tulgar |
| 2006/0206166 A1 | 9/2006 | Weiner |
| 2007/0073357 A1 | 3/2007 | Rooney et al. |
| 2007/0265675 A1 | 11/2007 | Lund et al. |
| 2007/0293914 A1 | 12/2007 | Woods et al. |
| 2008/0132961 A1 | 6/2008 | Jaax et al. |
| 2008/0172109 A1 | 7/2008 | Rahman et al. |
| 2008/0183236 A1 | 7/2008 | Gerber |
| 2009/0088816 A1 | 4/2009 | Harel et al. |
| 2009/0105785 A1 | 4/2009 | Wei et al. |
| 2009/0112291 A1 | 4/2009 | Wahlstrand et al. |
| 2009/0259273 A1 | 10/2009 | Figueiredo et al. |
| 2010/0076254 A1 | 3/2010 | Jimenez et al. |
| 2010/0076534 A1 | 3/2010 | Mock |
| 2010/0106231 A1* | 4/2010 | Torgerson .......... A61N 1/36082 607/116 |
| 2010/0114197 A1 | 5/2010 | Burnes et al. |
| 2010/0318167 A1 | 12/2010 | Conn et al. |
| 2011/0152959 A1 | 6/2011 | Sherwood et al. |
| 2011/0270269 A1 | 11/2011 | Swoyer et al. |
| 2011/0278948 A1 | 11/2011 | Forsell |
| 2011/0282416 A1 | 11/2011 | Hamann et al. |
| 2011/0301667 A1 | 12/2011 | Olson et al. |
| 2012/0016447 A1 | 1/2012 | Zhu et al. |
| 2012/0041512 A1 | 2/2012 | Weiner |
| 2012/0046712 A1 | 2/2012 | Woods et al. |
| 2012/0071950 A1 | 3/2012 | Archer |
| 2012/0119698 A1 | 5/2012 | Karalis et al. |
| 2012/0130448 A1 | 5/2012 | Woods et al. |
| 2012/0130465 A1 | 5/2012 | Risi et al. |
| 2012/0259381 A1 | 10/2012 | Smith et al. |
| 2012/0262108 A1 | 10/2012 | Olson et al. |
| 2012/0274270 A1 | 11/2012 | Dinsmoor et al. |
| 2012/0276854 A1 | 11/2012 | Joshi et al. |
| 2012/0276856 A1 | 11/2012 | Joshi et al. |
| 2013/0004925 A1 | 1/2013 | Labbe et al. |
| 2013/0006330 A1 | 1/2013 | Wilder et al. |
| 2013/0006331 A1 | 1/2013 | Weisgarber et al. |
| 2013/0023958 A1 | 1/2013 | Fell |
| 2013/0096651 A1 | 4/2013 | Ozawa |
| 2013/0150925 A1 | 6/2013 | Vamos et al. |
| 2013/0197608 A1 | 8/2013 | Eiger |
| 2013/0207863 A1 | 8/2013 | Joshi |
| 2013/0211479 A1 | 8/2013 | Olson et al. |
| 2013/0226266 A1 | 8/2013 | Murtonen et al. |
| 2013/0303942 A1 | 11/2013 | Damaser et al. |
| 2013/0310894 A1 | 11/2013 | Trier |
| 2013/0331909 A1 | 12/2013 | Gerber |
| 2014/0222112 A1 | 8/2014 | Fell |
| 2014/0237806 A1 | 8/2014 | Smith et al. |
| 2015/0214604 A1 | 7/2015 | Zhao et al. |

FOREIGN PATENT DOCUMENTS

| | | |
|---|---|---|
| EP | 1904153 | 4/2008 |
| EP | 2243509 | 10/2010 |
| JP | H0440966 A | 2/1992 |
| JP | 2003/047179 A | 2/2003 |
| JP | 2008512197 A | 4/2008 |
| JP | 2010088821 A | 4/2010 |
| JP | 2012508624 A | 4/2012 |
| JP | 2012510871 A | 5/2012 |
| JP | 2016/516554 | 6/2016 |
| WO | 2000/056677 A1 | 3/2000 |
| WO | 2000/066221 A1 | 11/2000 |
| WO | 2002/003408 A2 | 1/2002 |
| WO | 2004/103465 A1 | 12/2004 |
| WO | 2008/021524 | 2/2008 |
| WO | 2009/051539 A1 | 4/2009 |
| WO | 2009/091267 A2 | 7/2009 |
| WO | 2010/042056 A1 | 4/2010 |

(56) References Cited

FOREIGN PATENT DOCUMENTS

| WO | 2010/042057 A1 | 4/2010 |
|----|----------------|--------|
| WO | 2011/059565 | 5/2011 |
| WO | 2013/141884 | 9/2013 |
| WO | 2014/179811 | 11/2014 |

OTHER PUBLICATIONS

Bosch, J., et al., Sacral (S3) Segmental Nerve Stimulation as a Treatment for Urge Incontinence in Patients With Detrusor Instability: Results of Chronic Electrical Stimulation Using an Implantable Neural Prosthesis, The Journal of Urology, Aug. 1995, vol. 154, pp. 504-507.

Ghovanloo, M., et al., A Small Size Large Voltage Compliance Programmable Current Source for Biomedical Implantable Microstimulators, Proceedings of the 25th Annual International Conference of the IEEE EMBS, Sep. 17-21, 2003, pp. 1979-1982.

Tanagho, E., et al., Bladder Pacemaker: Scientific Basis and Clinical Future, Urology, Dec. 1982, vol. 20, No. 6, pp. 614-619.

Gundason, G., "A low-power ASK demodulator for Inductively coupled implantable electronics", Solid-State Circuits Conference, 2000, Esscirc 00, Proceedings of the 26RD European, IEEE, Sep. 19, 2000, pp. 385-388.

Humayun, M.S., et al., "A Variable Range Bi-Phasic Current Stimulus Driver Circuitry for an Implantable Retinal Prosthetic Device", IEEE Journal of Solid-State Circuits, IEEE Service Center, Piscataway, NJ, USA, vol. 40, No. 3, Mar. 1, 2005, (Mar. 1, 2005), pp. 763-771.

Van Paemel, M., "High-Efficiency Transmission for Medical Implants", IEEE Solid-State Circuits Magazine, IEEE, USA, vol. 3, No. 1, Jan. 1, 2011, pp. 47-59.

Wang, Chua-Chin, et al., "A 140-dB CMRR Low-noise Instrumentation Amplifier for Neural Signal Sensing", Circutis and Systems, 2006, APCCAS 2006, IEEE Asia Pacific Conference on IEEE, Piscataway, NJ, USA, Dec. 1, 2006 (Dec. 1, 2006), pp. 696-699.

\* cited by examiner

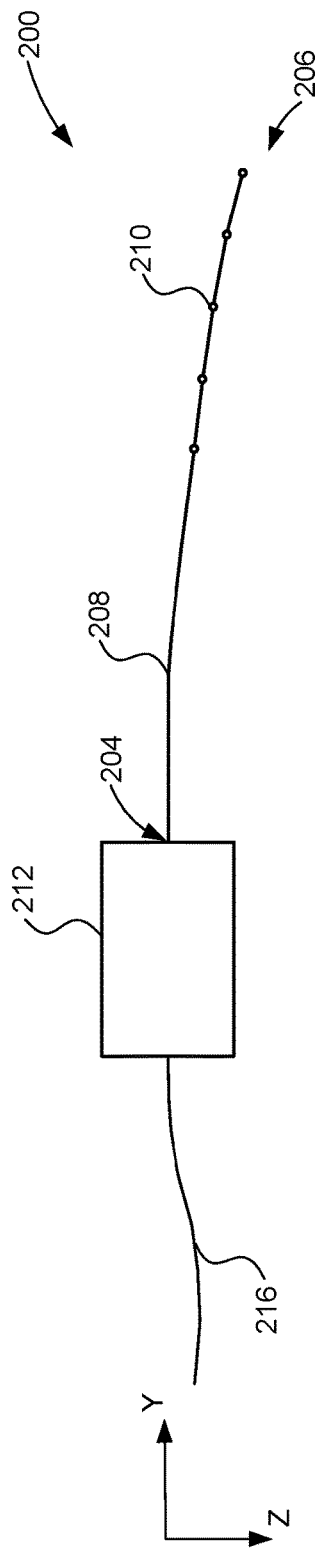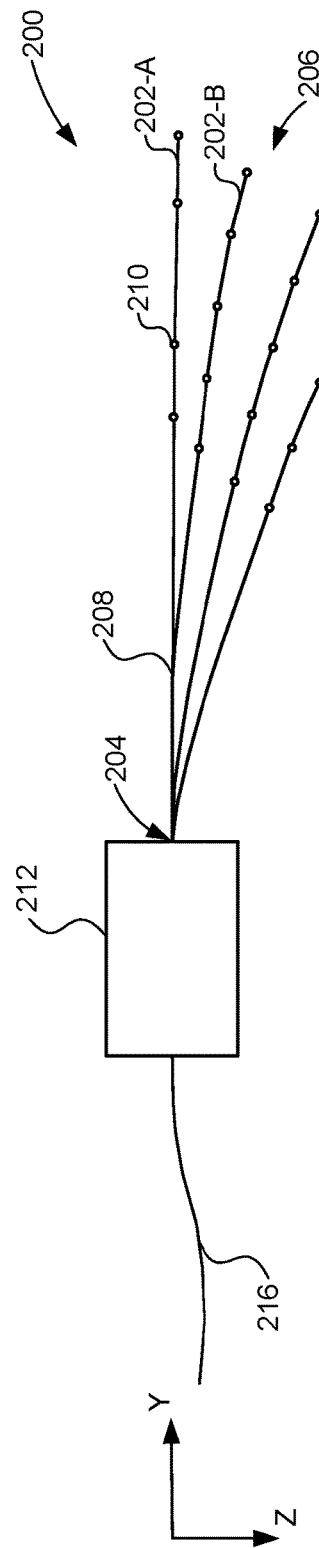
Fig. 2A
Fig. 2B

MULTI-BRANCH STIMULATION ELECTRODE FOR SUBCUTANEOUS FIELD STIMULATION

CROSS-REFERENCES TO RELATED APPLICATIONS

This application is a divisional of U.S. application Ser. No. 14/270,075 filed May 5, 2014, and entitled "MULTI-BRANCH STIMULATION ELECTRODE FOR SUBCUTANEOUS FIELD STIMULATION," which claims the benefit of U.S. Provisional Application No. 61/819,441 filed on May 3, 2013, the entire contents of each of which are hereby incorporated herein by reference for all purposes.

BACKGROUND

The prevalence of use of medical devices in treating ailments is increasing with time. In many instances, and as these medical devices are made smaller, these medical devices are frequently implanted within a patient. While the desirability of implantable devices is increasing as the size of the devices has decreased, the implantation process still frequently requires complicated surgery which can expose the patient to significant risks and protracted recovery times. In light of this, further methods, systems, and devices are desired to increase the ease of implantation of medical devices.

BRIEF SUMMARY

One aspect of the present disclosure relates to a neurostimulation system. The neurostimulation system includes an implantable pulse generator that can generate one or more non-ablative neurostimulation electrical signals, and a multi-branch electrode array that can be coupled to the pulse generator to thereby transmit the one or more non-ablative neurostimulation electrical signals to a nerve tissue. The multi-branch electrode array can include a plurality of branches. In some embodiments, at least some of the branches each include a plurality of electrode contacts. In some embodiments, when in a deployed configuration, the plurality of branches diverge away from one another such that distal tips of the branches are spaced farther apart than proximate portions of the branches. In some embodiments, when in the deployed configuration, the plurality of branches are in a substantially planar arrangement.

In some embodiment of the neurostimulation system, the plurality of branches are in a rake-shaped arrangement when in the deployed configuration. In some embodiments, the substantially planar arrangement comprises an arrangement in which the branches branch out across and curve downwardly from a reference plane. In some embodiments, the downward curve of the branches facilitates maintaining the branches in a subcutaneous tissue layer during deployment of the electrode array. In some embodiments, at least some of the branches include blunt dissecting distal tips.

In some embodiment of the neurostimulation system, the non-ablative neurostimulation electrical signals have a pulse amplitude of 0-1,000 mA. In some embodiments, the electrode array further can include a hub that can include features to allow anchoring of the hub to a tissue. In some embodiments, at least some of the electrode contacts are anode electrode contacts and wherein at least some of the electrode contacts are cathode electrode contacts. In some embodiments, of the electrodes on one branch are anode electrode contacts and all of the electrodes on an adjacent branch are cathode electrode contacts.

In some embodiment of the neurostimulation system, at least some of the branches include stiffening components that increase the stiffness of the branches to facilitate blunt dissecting by the branches. In some embodiments, the stiffening components can be a plurality of elongate members that can be connected by a stiffening element hub. In some embodiments, at least some of the branches can receive the stiffening elements.

In some embodiment of the neurostimulation system, the size of the electrode contacts varies as a function of position on at least some of the branches. The branches have a proximal end and a distal end. In some embodiments, the size of the electrode contact increases when the distance from the proximal end increases, or in other words, when the proximity of the electrode contact to the distal end of the branch increases. In some embodiments, some of the electrode contacts are each electrically connected to a resistive element. In some embodiments, the resistance of the resistive element increases when the proximity of the electrode contact to the proximal end of the branch increases.

One aspect of the present disclosure relates to an implantable electrode array system. The implantable electrode array system includes a multi-branch electrode array including a plurality of elongated branches that each include at least one electrode contact and a blunt dissecting distal tip, and an implantation cartridge for deploying the multi-branch electrode array from a retracted configuration to a deployed configuration. In some embodiments, the branches are retracted relative to the implantation cartridge when in the retracted configuration, and, wherein, the branches extend outwardly from the implantation cartridge a further distance than in the retracted configuration when in the deployed configuration. In some embodiments, the branches are arranged in a substantially planar fan-shaped arrangement when in the deployed configuration.

In some embodiments, at least some of the branches include stiffening components that increase the stiffness of the branches to facilitate blunt dissecting by the branches. In some embodiments, the stiffening components can include a plurality of elongate members that are connected by a stiffening element hub. In some embodiments, at least some of the branches can receive the stiffening elements. In some embodiments, the stiffening element can be a biodegradable outer layer on at least some of the branches. In some embodiment, at least some of the branches include an integrated stiffening element.

One aspect of the present disclosure relates to an implantable electrode array. The implantable electrode array includes a multi-branch electrode array including a plurality of elongated branches that each include at least one electrode contact and a blunt dissecting distal tip. In some embodiments, the branches are arranged in a substantially planar fan-shaped arrangement when in the deployed configuration.

In some embodiments, at least some of the branches include stiffening components that increase the stiffness of the branches to facilitate blunt dissecting by the branches. In some embodiments, the stiffening components can be a plurality of elongate members that are connected by a stiffening element hub. In some embodiments, at least some of the branches can receive the stiffening elements. In some embodiments, the stiffening element can be a biodegradable outer layer on at least some of the branches. In some embodiments, at least some of the branches include an integrated stiffening element.

One aspect of the present disclosure relates to a method of implanting a neurostimulation system. The method includes pushing a plurality of branches of an electrode array into a subcutaneous tissue including or proximate nerve tissue such that distal tips of the plurality of branches pierce through the subcutaneous tissue and such that the plurality of branches fan outwardly into a substantially planar fan-shaped arrangement, and connecting the electrode array to a neurostimulation pulse generator that can stimulate the nerve tissue.

In some embodiments, the method can further include inserting an implantation cartridge through an incision. In some embodiments, the implantation cartridge holds the plurality of branches of the electrode array. In some embodiments, the method includes separating the plurality of branches from the implantation cartridge and extracting the implantation cartridge from the incision. The method can include, removing a stiffening element from at least one of the branches. In some embodiments, the method includes plugging any void left by the removing of the stiffening element from the at least one of the branches.

Further areas of applicability of the present disclosure will become apparent from the detailed description provided hereinafter. It should be understood that the detailed description and specific examples, while indicating various embodiments, are intended for purposes of illustration only and are not intended to necessarily limit the scope of the disclosure.

BRIEF DESCRIPTION OF THE DRAWINGS

FIGS. 2A and 2B are side views of embodiments of the multi-branch stimulation electrode shown in FIG. 2.

Figure 1:
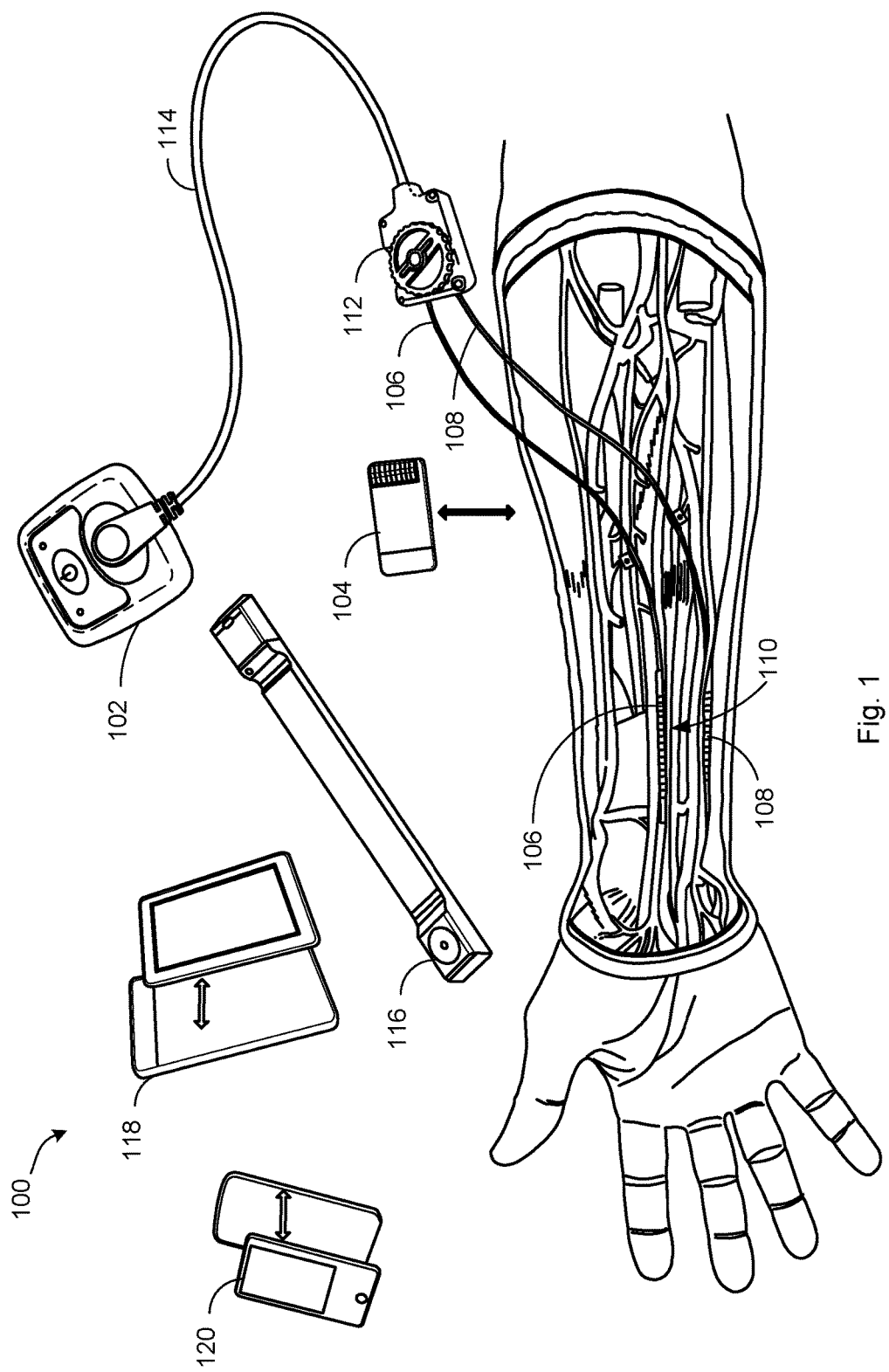
FIG. 1 is a schematic illustration of one embodiment of an implantable neurostimulation system.

In the appended figures, similar components and/or features may have the same reference label. Where the reference label is used in the specification, the description is applicable to any one of the similar components having the same reference label.

DETAILED DESCRIPTION OF THE FIGURES

A significant percentage of the Western (EU and US) population is affected by Neuropathic pain (chronic intractable pain due to nerve damage). In many people, this pain is severe. There are thousands of patients that have chronic intractable pain involving a nerve. Neuropathic pain can be very difficult to treat with only half of patients achieving partial relief. Thus, determining the best treatment for individual patients remains challenging. Conventional treatments include certain antidepressants, anti-epileptic drugs and opioids. However, side effects from these drugs can be detrimental. In some of these cases, electrical stimulation, including FES, can provide effect treatment of this pain without the drug-related side effects.

A spinal cord stimulator is a device used to deliver pulsed electrical signals to the spinal cord to control chronic pain. Because electrical stimulation is a purely electrical treatment and does not cause side effects similar to those caused by drugs, an increasing number of physicians and patients favor the use of electrical stimulation over drugs as a treatment for pain. The exact mechanisms of pain relief by spinal cord stimulation (SCS) are unknown. Early SCS trials were based the Gate Control Theory, which posits that pain is transmitted by two kinds of afferent nerve fibers. One is the larger myelinated Aδ fiber, which carries quick, intense-pain messages. The other is the smaller, unmyelinated "C" fiber, which transmits throbbing, chronic pain messages. A third type of nerve fiber, called Aβ, is "non-nociceptive," meaning it does not transmit pain stimuli. The gate control theory asserts that signals transmitted by the Aδ and C pain fibers can be thwarted by the activation/stimulation of the non-nociceptive Aβ fibers and thus inhibit an individual's perception of pain. Thus, neurostimulation provides pain relief by blocking the pain messages before they reach the brain.

SCS is often used in the treatment of failed back surgery syndrome, a chronic pain syndrome that has refractory pain due to ischemia. SCS complications have been reported in a large portion, possibly 30% to 40%, of all SCS patients. This increases the overall costs of patient pain management and decreases the efficacy of SCS. Common complications include: infection, hemorrhaging, injury of nerve tissue, placing device into the wrong compartment, hardware malfunction, lead migration, lead breakage, lead disconnection, lead erosion, pain at the implant site, generator overheating, and charger overheating. The occurrence rates of common complications are surprisingly high: including lead extension connection issues, lead breakage, lead migration and infection.

Peripheral neuropathy, another condition that can be treated with electrical stimulation, may be either inherited or acquired. Causes of acquired peripheral neuropathy include physical injury (trauma) to a nerve, viruses, tumors, toxins, autoimmune responses, nutritional deficiencies, alcoholism, diabetes, and vascular and metabolic disorders. Acquired peripheral neuropathies are grouped into three broad categories: those caused by systemic disease, those caused by trauma, and those caused by infections or autoimmune disorders affecting nerve tissue. One example of an acquired peripheral neuropathy is trigeminal neuralgia, in which damage to the trigeminal nerve (the large nerve of the head and face) causes episodic attacks of excruciating, lightning-like pain on one side of the face.

A high percentage of patients with peripheral neuropathic pain do not benefit from SCS for various reasons. However, many of these patients can receive acceptable levels of pain relief via direct electrical stimulation to the corresponding peripheral nerves. This therapy is called peripheral nerve stimulation (PNS). As FDA approved PNS devices have not been commercially available in the US market, Standard spinal cord stimulator (SCS) devices are often used off label by pain physicians to treat this condition. A significant portion of SCS devices that have been sold may have been used off-label for PNS.

As current commercially-available SCS systems were designed for stimulating the spinal cord and not for peripheral nerve stimulation, there are more device complications associated with the use of SCS systems for PNS than for SCS. Current SCS devices (generators) are large and bulky. In the event that an SCS is used for PNS, the SCS generator is typically implanted in the abdominal or in the lower back above the buttocks and long leads are tunneled across multiple joints to reach the target peripheral nerves in the arms, legs or face. The excessive tunneling and the crossing of joints leads to increased post-surgical pain and higher device failure rates. Additionally, rigid leads can lead to skin erosion and penetration, with lead failure rates being far too high within the first few years of implantation. Many or even most complications result in replacement surgery and even multiple replacement surgeries in some cases.

One embodiment of an implantable neurostimulation system 100 is shown in FIG. 1, which implantable neurostimulation system 100 can be, for example, a peripherally-implantable neurostimulation system 100. In some embodiments, the implantable neurostimulation system 100 can be used in treating patients with, for example, chronic, severe, refractory neuropathic pain originating from peripheral nerves. In some embodiments, the implantable neurostimulation system 100 can be used to either stimulate a target peripheral nerve or the posterior epidural space of the spine.

The implantable neurostimulation system 100 can include one or several pulse generators. The pulse generators can comprise a variety of shapes and sizes, and can be made from a variety of materials. In some embodiments, the one or several pulse generators can generate one or several non-ablative electrical pulses that are delivered to a nerve to control pain. In some embodiments, these pulses can have a pulse amplitude of between 0-1,000 mA, 0-100 mA, 0-50 mA, 0-25 mA, and/or any other or intermediate range of amplitudes. One or more of the pulse generators can include a processor and/or memory. In some embodiments, the processor can provide instructions to and receive information from the other components of the implantable neurostimulation system 100. The processor can act according to stored instructions, which stored instructions can be located in memory, associated with the processor, and/or in other components of the content injection system 100. The processor can, in accordance with stored instructions, make decisions. The processor can comprise a microprocessor, such as a microprocessor from Intel® or Advanced Micro Devices, Inc.®, or the like.

In some embodiments, the stored instructions directing the operation of the processor may be implemented by hardware, software, scripting languages, firmware, middleware, microcode, hardware description languages, and/or any combination thereof. When implemented in software, firmware, middleware, scripting language, and/or microcode, the program code or code segments to perform the necessary tasks may be stored in a machine readable medium such as a storage medium. A code segment or machine-executable instruction may represent a procedure, a function, a subprogram, a program, a routine, a subroutine, a module, a software package, a script, a class, or any combination of instructions, data structures, and/or program statements. A code segment may be coupled to another code segment or a hardware circuit by passing and/or receiving information, data, arguments, parameters, and/or memory contents. Information, arguments, parameters, data, etc. may be passed, forwarded, or transmitted via any suitable means including memory sharing, message passing, token passing, network transmission, etc.

In some embodiments, the memory of one or both of the pulse generators can be the storage medium containing the stored instructions. The memory may represent one or more memories for storing data, including read only memory (ROM), random access memory (RAM), magnetic RAM, core memory, magnetic disk storage mediums, optical storage mediums, flash memory devices and/or other machine readable mediums for storing information. In some embodiments, the memory may be implemented within the processor or external to the processor. In some embodiments, the memory can be any type of long term, short term, volatile, nonvolatile, or other storage medium and is not to be limited to any particular type of memory or number of memories, or type of media upon which memory is stored. In some embodiments, the memory can include, for example, one or both of volatile and nonvolatile memory. In one specific embodiment, the memory can include a volatile portion such as RAM memory, and a nonvolatile portion such as flash memory.

In some embodiments, one of the pulse generators can be an external pulse generator 102 or an implantable pulse generator 104. The external pulse generator 102 can be used to evaluate the suitability of a patient for treatment with the implantable neurostimulation system 100 and/or for implantation of an implantable pulse generator 104.

In some embodiments, one of the pulse generators can be the implantable pulse generator 104, which can be sized and shaped, and made of material to allow implantation of the implantable pulse generator 104 inside of a body. In some embodiments, the implantable pulse generator 104 can be sized and shaped so as to allow placement of the implantable pulse generator 104 at any desired location in a body, and in some embodiments, placed proximate to a peripheral nerve such that leads (discussed below) are not tunneled across joints and/or such that extension cables are not needed.

In some embodiments, the electrical pulses generated by the pulse generator can be delivered to one or several nerves 110 and/or to tissue proximate to one or several nerves 110 via one or several leads. The leads can include conductive portions, such as electrodes or contact portions of electrodes, and non-conductive portions. The leads can have a variety of shapes, can be in a variety of sizes, and can be made from a variety of materials, which size, shape, and materials can be dictated by the application or other factors.

In some embodiments, the leads can include an anodic lead 106 and/or a cathodic lead 108. In some embodiments, the anodic lead 106 and the cathodic lead 108 can be identical leads, but can receive pulses of different polarity from the pulse generator.

In some embodiments, the leads can connect directly to the pulse generator, and in some embodiments, the leads can be connected to the pulse generator via a connector 112 and a connector cable 114. The connector 112 can comprise any device that is able to electrically connect the leads to the connector cable 114. Likewise, the connector cable can be any device capable of transmitting distinct electrical pulses to the anodic lead 106 and the cathodic lead 108.

In some embodiments, the implantable neurostimulation system 100 can include a charger 116 that can be configured to recharge the implantable pulse generator 104 when the implantable pulse generator 104 is implanted within a body. The charger 116 can comprise a variety of shapes, sizes, and features, and can be made from a variety of materials. Like the pulse generators 102, 104, the charger 116 can include a processor and/or memory having similar characteristics to those discussed above. In some embodiments, the charger 116 can recharge the implantable pulse generator 104 via an inductive coupling.

In some embodiments, one or several properties of the electrical pulses can be controlled via a controller. In some embodiments, these properties can include, for example, the frequency, strength, pattern, duration, or other aspects of the timing and magnitude of the electrical pulses. In one embodiment, these properties can include, for example, a voltage, a current, or the like. In one embodiment, a first electrical pulse can have a first property and a second electrical pulse can have a second property. This control of the electrical pulses can include the creation of one or several electrical pulse programs, plans, or patterns, and in some embodiments, this can include the selection of one or several pre-existing electrical pulse programs, plans, or patterns. In the embodiment depicted in FIG. 1, the implantable neurostimulation system 100 includes a controller that is a clinician programmer 118. The clinician programmer 118 can be used to create one or several pulse programs, plans, or patterns and/or to select one or several of the created pulse programs, plans, or patterns. In some embodiments, the clinician programmer 118 can be used to program the operation of the pulse generators including, for example, one or both of the external pulse generator 102 and the implantable pulse generator 104. The clinician programmer 118 can comprise a computing device that can wiredly and/or wirelessly communicate with the pulse generators. In some embodiments, the clinician programmer 118 can be further configured to receive information from the pulse generators indicative of the operation and/or effectiveness of the pulse generators and the leads.

In some embodiments, the controller of the implantable neurostimulation system 100 can include a patient remote 120. The patient remote 120 can comprise a computing device that can communicate with the pulse generators via a wired or wireless connection. The patient remote 120 can be used to program the pulse generator, and in some embodiments, the patient remote 120 can include one or several pulse generation programs, plans, or patterns created by the clinician programmer 118. In some embodiments, the patient remote 120 can be used to select one or several of the pre-existing pulse generation programs, plans, or patterns and to select, for example, the duration of the selected one of the one or several pulse generation programs, plans, or patterns.

Advantageously, the above outlined components of the implantable neurostimulation system 100 can be used to control and provide the generation of electrical pulses to mitigate patient pain.

Figure 2:
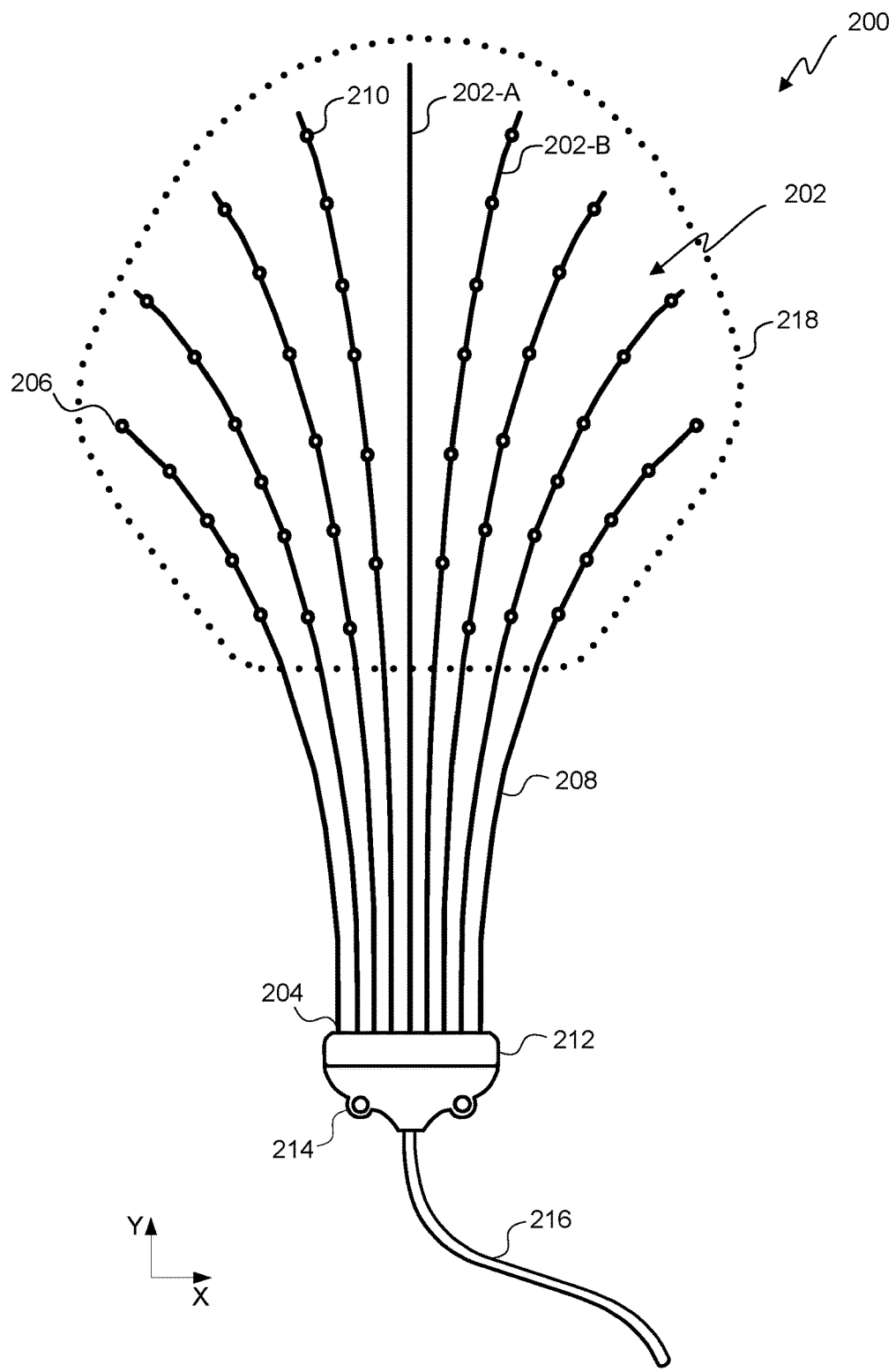
FIG. 2 is a top view of one embodiment of a multi-branch stimulation electrode.

With reference now to FIG. 2, a schematic illustration of one embodiment of a multi-branch stimulation electrode 200, also referred to herein as a multi-branch electrode array, is shown. In some embodiments, the multi-branch stimulation electrode 200 can be used in the place of one or both of leads 106, 108 shown in FIG. 1. In some embodiments, the multi-branch stimulation electrode 200 can advantageously enable treatment of a broader area than treated by use of leads 106, 108. Specifically, in some embodiments, the multi-branch stimulation electrode 200 can enable peripheral field stimulation (PFS). In some embodiments, PFS includes the treatment of an area of pain or an area of referred pain. In some embodiments, this pain is not associated with an identified nerve. In contrast to PNS in which a specific nerve is identified and targeted, PFS can include stimulation of a broad area as no specific nerve is identified and targeted.

In one embodiment, for example, the broader area treatment enabled by the multi-branch stimulation electrode 200 can ease placement of the multi-branch stimulation electrode 200 with respect to the nerve as the exact placement of the multi-branch stimulation electrode 200 is less important than in the case of leads 106, 108. The multi-branch stimulation electrode 200 can, in some embodiments, be placed in subcutaneous tissue such as, for example, the layer of subcutaneous adipose tissue located between muscle and the epidermis.

The multi-branch stimulation electrode 200 can include a plurality of branches 202. In some embodiments, the branches 202 can be configured to deliver one or several electric pulses to tissue of the patient. In some embodiments, the branches 202 can comprise a variety of shapes and sizes and can be made from a variety of materials. In the embodiment depicted in FIG. 2, the branches 202 comprise a plurality of the elongate members that have a proximal end 204 and a distal end 206.

Multi-branch stimulation electrode 200 can have any desired number of branches including, for example, an even number of branches 202 or an odd number of branches 202. In some embodiments, the multi-branch stimulation electrode can have, for example, 2 branches 202, 3 branches 202, 4 branches 202, 5 branches 202, 6 branches 202, 7 branches 202, 8 branches 202, 9 branches 202, 10 branches 202, 11 branches 202, 12 branches 202, 15 branches 202, 20 branches 202, 50 branches 202, and/or any other or intermediate number of branches. In some embodiments, some of the branches 202 can be an anodic branches, and some of the branches 202 can be cathodic branches. In some embodiments, the branches 202 can alternate between anodic and cathodic branches such that the adjacent branches 202 to an anodic branch are cathodic branches and the adjacent branches to a cathodic branch are anodic branches. Alternatively, in some embodiments, some or all of the branches can include one or several stimulation contacts that can be anodic stimulation contacts, and some or all of the branches can include one or several stimulation contacts that can be cathodic stimulation contacts. In some embodiments, these stimulation contacts can alternate such that an anodic stimulation contact is adjacent to cathodic stimulation contacts, and such that cathodic stimulation contacts are adjacent to anodic stimulation contacts. Advantageously, by alternating between an anodic and a cathodic branch, and/or alternating between anodic and cathodic stimulation contacts, the creation of circuits through the patient's tissue to allow transmission of electric pulses can be facilitated. In some instances, the system is designed to re-configure one or more of the branches between anodic or cathodic configurations and/or one or more of the stimulation contacts between anodic or cathodic configurations.

In some embodiments, each of the branches 202 can be the same size, have the same shape, and be made from the same material, and in some embodiments, some of the branches 202 can have one of a different size, shape, or material than others of the branches 202. For example, in the embodiment depicted in FIG. 2, a first branch 202-A, located along a central axis of the multi-branch stimulation electrode 200, is longer than a second branch 202-B, located adjacent to the central access of the multi-branch stimulation electrode 200. In the embodiment depicted in FIG. 2, the first branch 202-A extends parallel to a y-axis such that the distal end 206 is farther in the positive y-direction than the proximal end 204. As further seen in FIG. 2, the first branch 202-A extends perpendicular to the x-axis, and the second branch 202-B is farther in the positive x-direction than the first branch 202-A. Although not shown, the multi-branch stimulation electrode 200 can be further defined by the z-axis which extends from the intersection of the x- and y-axes according to the right-hand rule.

In the embodiment depicted in FIG. 2, the branches 202 can be spaced apart from each other. In some embodiments, the branches 202 can be spaced apart from each other such that branches 202 extend parallel to each other, and in some embodiments, the branches can be spaced apart such that the branches 202 are non-parallel to each other. As described further below, in some instances, the spacing and arrangement of the branches will vary depending on whether the electrode array is in a deployed or non-deployed configuration. In some embodiments, the branches 202 can be spaced in a fan or rake-shaped arrangement, wherein the proximal ends 204 of the branches 202 are spaced more closely to each other than are the distal ends 206 of the branches. In some embodiments, the nonparallel extension of the branches 202 (when in a deployed configuration) can result in changing spacing between the branches. Specifically, in the embodiment depicted in FIG. 2, the spacing between the branches 202 increases when moving in the positive y-direction (towards the top of the page) from the proximal end 204 to the distal end 206 of any of the branches 202. In some embodiments, some or all of the branches 202 can be each located in a single plane along the z-axis (e.g. in a plane defined by or parallel to the page of FIG. 2) and in some embodiments, one or several of the branches 202 can be located in multiple planes along the z-axis, and/or extend through multiple planes along the z-axis. In some embodiments, the position of the branches 202 along the z-axis can serve to match the shape of the multi-branch stimulation electrode 202, for example, a curved body part into which the multi-branch stimulation electrode 202 is being implanted. In one embodiment in which the multi-branch stimulation electrode 202 is configured for being implanted in, for example, a limb, the position of a point on one or several of the branches 202 in the z-axis can vary as a function of, for example position on the y-axis and/or on the x-axis. In some embodiments, the shaping of the multi-branch stimulation electrode 202 in the z-axis can facilitate maintaining the multi-branch stimulation electrode 200 in the subcutaneous tissue. In one embodiment, for example, the position of a point on one or several of the branches 202 z-axis can vary as a function of distance in the x-axis from the first branch 202-A.

In the particular embodiment of FIG. 2, the branches 202 of the electrode array are in a substantially planar arrangement, although the branches 202 are not entirely located in a single plane. As shown in FIG. 2A, which shows the electrode array of FIG. 2 in a side view, all of the branches 202 curve slightly downwardly towards distal tips of the branches 202, which facilitates maintaining the branches 202 in a subcutaneous layer of tissue during implantation and insertion, as described further below. As shown in FIG. 2B, which shows another embodiment of the electrode array of FIG. 2 in a side view, some of the branches 202 curve slightly downwardly towards distal tips of the branches 202, which facilitates maintaining the branches 202 in a subcutaneous layer of tissue during implantation and insertion, as described further below. In some embodiments, the branches 202 curve downwardly such that the distal tips are approximately 0.5 mm, 1 mm, 2 mm, 3 mm, 5 mm, 10 mm, 15 mm, and/or any other or intermediate distance below proximal ends of the branches.

As the spacing between the branches 202 changes, the spacing between the conductive portions of the branches 202, which may be stimulation contacts or electrode contacts, changes. This change in the distance between the conductive portions of the branches 202 changes one or several of the electrical properties, which can be, for example, impedance, of the circuit extending from one of the conductive portions of one branch to another conductive portion of another branch. In some embodiments, differences in electrical properties of circuits extending from different conductive portions of different branches to each other affects the ability of the implantable neurostimulation system 100 to provide desired stimulation to a nerve and/or area.

In some embodiments, for example, in which the electrical property is an impedance, different impedances for different circuits can result in more current passing through some circuits and less current passing through others. This can disadvantageously result in unequal stimulation across an area and of a nerve which can inhibit the ability of the implantable neurostimulation system 100 to treat pain and/or to stimulate a nerve. In some embodiments, the multi-branch stimulation electrode 200 can include one or several features configured to counteract the effects of differential spacing between conductive portions of different branches such that the electrical properties of these circuits are the same and/or approximately the same. In some embodiments, the electrical properties of the circuits are approximately the same when they vary by less than 40%, 30%, 20%, 10%, 5%, 1%, or any other or intermediate percent from each other.

In some embodiments, some or all of the branches 202 can include a body 208. The body 208 can comprise a variety of shapes and sizes and can be made from a variety of materials. In some embodiments, the body 208 can extend the entire length of the branch 202, and in some embodiments, the body can extend a portion of the length of the branch 202. In some embodiments, the body 208 can be approximately cylindrical when the body 208 is positioned to extend in a straight line and body 208 can have a circular cross-section.

In some embodiments, the body 208 can be rigid, flexible, and/or elastic. In some embodiments, the properties of the body 208 can facilitate the implantation of the body 208 and decrease problems caused by the implantation of the body 208. In some embodiments, the body 208 can be more easily implanted when it is rigid. In some embodiments, the body 208 is less likely to cause negative side effects when the body 208 is flexible and/or elastic. In some embodiments, the body 208 can be made of a material that is rigid at a first, pre-insertion temperature and flexible at a second, body temperature. In some embodiments, such material can be rigid during the implantation process but can, as the body 208 warms to body temperature, become flexible. In such an embodiment, the body can have an "integrated stiffening element." Properties of some aspects of stiffening elements will be discussed at greater lengths below. In some embodiments, the body 208 can include, for example, a rigid, biodegradable outer coating and a flexible, inner portion. In such an embodiment, the rigid, biodegradable outer coating can biodegrade after the implantation of the body 208 to leave the flexible, inner portion of the body 208. In some embodiments, the body 208 can comprise a flexible member and a stiffening member, which can be, for example, a pre-formed stiffening member, can be inserted into the body 208 to facilitate implantation. In such an embodiment, after the body 208 has been implanted, the stiffening member can be removed.

In some embodiments, the bodies 208 of the branches 202 can comprise a biocompatible material. In some embodiments, the bodies 208 of the branches 202 can comprise, for example, a natural material, a man-made material, a polymer, a metal or metal alloy, or the like. In some embodiments, the material of the body 208 can be selected so as to be flexible at a body temperature and to be rigid or semi rigid at room temperature.

In some embodiments, some or all of the branches 202 can include one or several stimulation contacts 210 that can be, for example, located at positions along the body 208 of the therewith associated branch 202. The one or several stimulation contacts 210 can be configured to pass one or several electrical pulses to a portion of the patient's tissue. In some embodiments, the stimulation contacts 210 can comprise a conductive material that can form, for example, a peripheral band around one or several portions of the body 208. In some embodiments, the stimulation contacts 206 can radially extend beyond the outside edge of the body 204 so as not to be flush with the body 204, and in some embodiments, the stimulation contacts 206 can be flush with the body 204.

The stimulation contacts 210 on a single branch 202 can be spaced apart. In some embodiments, each of the stimulation contacts 210 can be equally spaced along the body 208 of the branch 202, and in some embodiments, the stimulation contacts 210 can be unequally spaced and/or unevenly spaced along the body 208 of the branch 202.

The stimulation contacts 210 can comprise a variety of shapes and sizes and can be made from a variety of materials. In some embodiments, each of the stimulation contacts 210 can comprise the same size and/or shape, and in some embodiments, some or all of the stimulation contacts 210 can comprise different sizes and/or shapes. In some embodiments, the size, shape, and/or material of some or all of the stimulation contacts 210 can be selected based on desired effect on one or several electrical properties of the completed circuit including to stimulation contacts 210 and a portion of the patient tissue. In one embodiment, for example, the size of the stimulation contacts 210 can increase as the distance of the stimulation contact 210 from the proximal end 204 of the branch increases.

In some embodiments, the stimulation contacts 210 can have similar and/or the same material properties as the material of the body 208. Advantageously the matching and/or pairing of the material properties of the stimulation contacts 210 and the body 208 can decrease stresses that may arise in the one or both of the body 208 and the stimulation contacts 210 during implantation of the multi-branch stimulation electrode 200 in the body of a patient.

In some embodiments, and as seen in FIG. 2, the proximal ends 204 of the branches 202 connect to hub 212. The hub 212 can comprise a variety of shapes and sizes and can be made from a variety of materials. In some embodiments, the hub 212 can comprise a biocompatible outer housing and/or can be made up one or several biocompatible materials. In some embodiments, the housing of the hub 212 can comprise an interior housing and/or an exterior housing. In some embodiments, the interior housing of the hub 212 can be rigid and the exterior of the hub 212 can be flexible and/or deformable. Advantageously, a flexible and/or deformable exterior housing of the hub 212 can decrease irritation that may arise from implanting the hub 212 in the patient's body.

The branches 202 can connect to the hub 212 in many ways. In some embodiments, the connections of the branches 202 to the hub 212 can be within a single plane in the Z axis, and in some embodiments, the connections of the branches 202 to the hub 212 can be in multiple planes in the z-axis. In some embodiments, the connections of the branches 202 to the hub 212 can be spaced along the x-axis and can, for example, be equally spaced along the x-axis. In some embodiments, the hub 212, including the connection points of the branches 202 to the hub 212, can be sealed so as to decrease the likelihood of bacterial growth within and/or associated with the hub 212.

The hub 212 can include one or several anchor features 214 that can be used to secure and/or fix the position of the hub 212 in the patient's body. In the embodiment depicted in FIG. 2, these anchor features 214 comprise suture eyelets that can be used in suturing the hub to tissue within the patient's body.

The hub 212 can connect to lead 216, which lead 216 can connect to one of the pulse generators 102, 104. Hub 212 can include one or several conductors that are electrically connected with one or several of the stimulation contacts 210 of the branches 202. These one or several conductors can be used to conduct electrical pulses from the pulse generator 102, 104 to the stimulation contacts 210. In some embodiments, the one or several conductors can be enclosed in an insulative, biocompatible shell. In some embodiments, the conductors and the biocompatible shell can be flexible and/or rigid, can comprise a variety of shapes and sizes, and can be made from a variety of materials.

Figure 3:
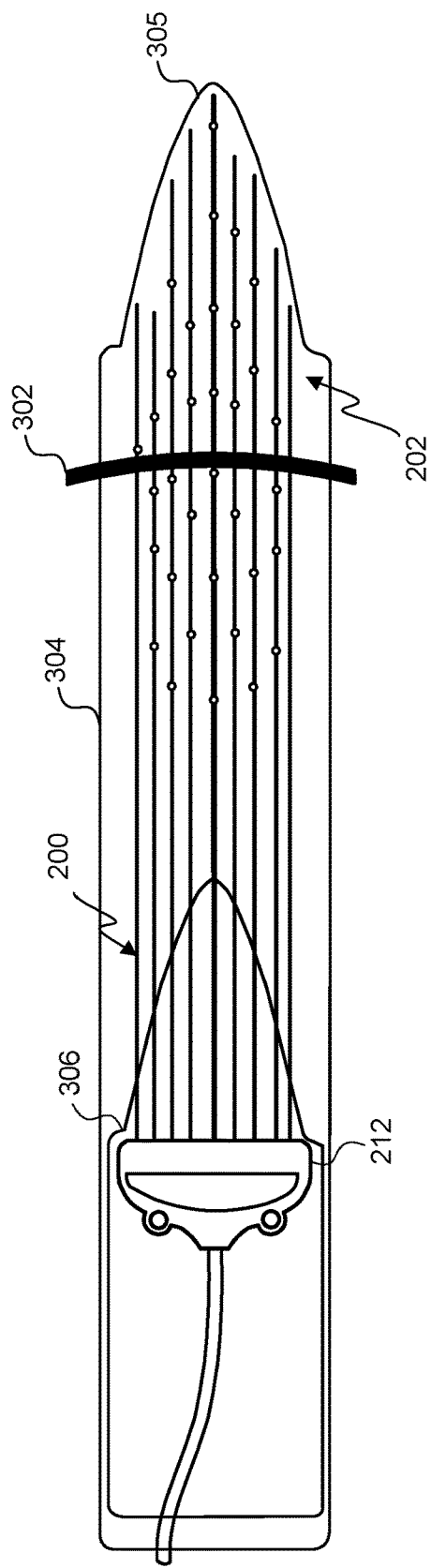
FIG. 3 is a top view of one embodiment of an implantation system including the multi-branch stimulation electrode.

With reference now to FIG. 3, a schematic illustration of one embodiment of an implantation system 300 is shown. In some embodiments, the implantation system 300 can be used to implant the multi-branch stimulation electrode 200 in a patient's body. The components of the implantation system 300 can comprise a variety of shapes and sizes and can be made from a variety of materials. In some embodiments, the components of the implantation system 300 and the implantation system 300 as a whole can be sized and shaped to allow insertion of portions of the implantation system 300 through an incision 302. As seen in FIG. 3, the implantation system includes the multi-branch stimulation electrode 200 including, the leads 202, and the hub 212.

The implantation system 300 can include an implantation cartridge 304 that can include an insertion tip 305. The insertion tips 305, also referred to herein as a piercing tip, can be configured to pierce tissue of the patient. The implantation cartridge 304 can comprise a variety of shapes and sizes and can be made of a variety of materials. In some embodiments, for example, the insertion tip 305 of the implantation cartridge 304 can extend to a point where a rounded tip and/or can taper to a point or a rounded tip. In some embodiments, the point or rounded tip can be inserted into the patient's body through the incision 302 and can ease the insertion of the implantation cartridge 304 through the incision 302.

In some embodiments, the implantation cartridge 304 can comprise an elongate member having a U-shaped cross-section with a bottom and sides extending in the same direction from the bottom. This bottom and sides of the implantation cartridge 304 partially bound an internal volume of the implantation cartridge 304. In some embodiments, the other components of the implantation system 300 can be held within and/or retained within the internal volume of the implantation cartridge 304.

In some embodiments, the implantation cartridge 304 can be configured to house the multi-branch stimulation electrode 200 and hold the branches 202 of the multi-branch stimulation electrode 200 in a first, insertion position. As depicted in FIG. 3, the branches 202, which can be, for example, pre-formed branches of the multi-branch stimulation electrode 200 that are held parallel to each other in the first, insertion position. The implantation cartridge 304 can include features configured to hold the branches 202 of the multi-branch stimulation electrode 200 and the first, insertion position. In one embodiment, for example, the features configured to hold the branches 202 of multi-branch stimulation electrode 200 in the first, insertion position can comprise a comb-shaped guide. In one such embodiment, one or several of the branches 202 of the multi-branch stimulation electrode 200 can be held between teeth of the comb-shaped guide. In such an embodiment, the teeth of the comb shaped guide can extend in the same direction as the sides such that the comb shaped guide and the implantation cartridge 304 can be lifted off of the multi-branch stimulation electrode 200 after implantation of the multi-branch stimulation electrode 200 in the patient's body.

The implantation system 300 can include an insertion sleigh 306. In some embodiments, the insertion sleigh can fit within the internal volume of the implantation cartridge 304 and can be slidable towards and away from the insertion tip 305 of the implantation cartridge 304. In some embodiments, the insertion sleigh 304 can engage with, for example, some or all of the multi-branch stimulation electrode 200 such as, for example, the hub 212 to allow insertion of and/or implantation of the multi-branch stimulation electrode 200 when the insertion sleigh 304 is moved towards the insertion tip 305 of the implantation cartridge 304.

Figure 4A:
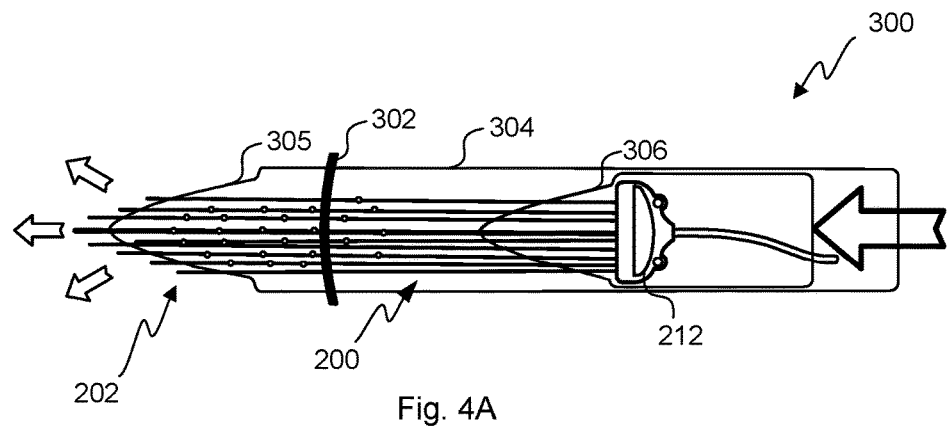
FIGS. 4A-4C depict one embodiment of a process for implanting a multi-branch stimulation electrode.
Figure 4B:
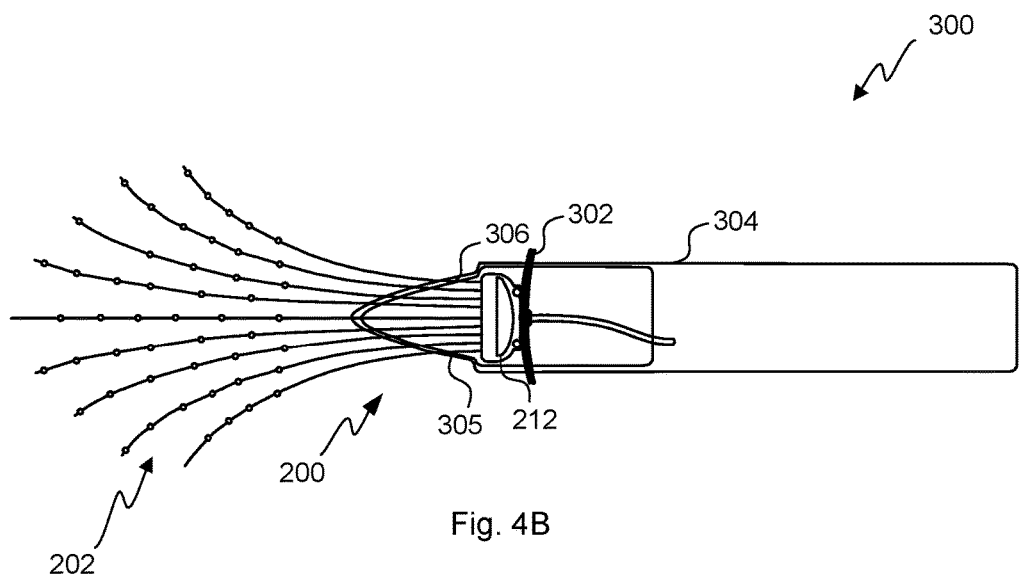
Figure 4C:
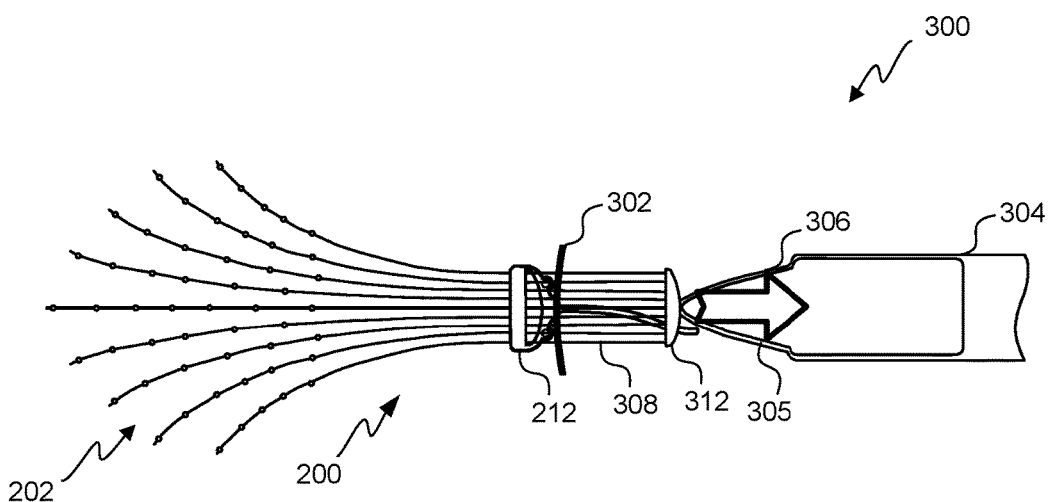

With reference now to FIGS. 4A, 4B, and 4C a schematic illustration of one embodiment of a process for the implantation of the multi-branch stimulation electrode 200 is shown. The process begins in FIG. 4A, wherein the insertion tip 305 of the insertion cartridge 304 is inserted through the incision 302 in the patient's body.

After the insertion cartridge 304 is placed in the desired position, the insertion sleigh 306 is displaced towards the insertion tip 305 of the insertion cartridge 304. As the insertion sleigh 306 is displaced towards the insertion tip 305 of the insertion cartridge 304, the branches 202 of the multi-branch stimulation electrode 200 penetrate into the tissue of the patient and move towards a second, implanted position. In some embodiments, the branches 202 of the multi-branch stimulation electrode 200 have a desired spacing and distribution when they reach the second, implanted position.

FIG. 4B depicts one embodiment of the implantation system 300 after the branches 202 of the multi-branch stimulation electrode 200 have reached the second, implanted position. As seen, the branches 202 of the multi-branch stimulation electrode 200 have reached the second, implanted position when the insertion sleigh 306 has reached the insertion 305 of the insertion cartridge 304 and when the hub 212 of the multi-branch stimulation electrode is inserted through the incision 302.

After the branches 202 of the multi-branch stimulation electrode 200 have reached the second, implanted position, and after the multi-branch stimulation electrode 200, including the branches 202 have reached a desired position, the insertion sleigh 306 and the insertion cartridge 304 are separated from the multi-branch stimulation electrode and removed from the patient's body out of the insertion 302 as is depicted in FIG. 4C. In some embodiments, after the separation of the multi-branch stimulation electrode 200 from the insertion sleigh 306 and the insertion cartridge 304, the multi-branch stimulation electrode 200 can be secured with respect to the incision 302 and/or with respect to the patient's body. In some embodiments, the multi-branch stimulation electrode 200 can be secured with respect to the patient's body via the anchor features 214 of the hub 212.

After the multi-branch stimulation electrode has been secured within the patient's body, and as further depicted in FIG. 4C, the stiffening elements 308, if the multi-branch stimulation electrode 200 includes stiffening elements 308, can be withdrawn. In some embodiments, the stiffening elements 308 can provide rigidity to the branches 202 of the multi-branch stimulation electrode 200 to allow penetration of the branches 202 into and through tissue of the patient's body, and in some embodiments, the stiffening elements 308 can bias the branches 202 of the multi-branch stimulation electrode 200 towards the second, implanted position. After the branches 202 have reached the desired position, the stiffening elements 308 can be withdrawn from the branches 202 so the branches 202 have a desired level of flexibility. In some embodiments, the stiffening members 308 can be connected to a stiffening element hub 310 and the stiffening members 308 can be withdrawn from the branches 202 of multi-branch stimulation electrode 200 by withdrawing the stiffening element hub 310 from the hub 212 and out of and through the incision 302. In the event that the withdrawal of the stiffening members 308 created one or several voids or cavities within one or both of the hub 212 and the branches 202, the one or several voids or cavities can be sealed, plugged, and/or filled.

Figure 5:
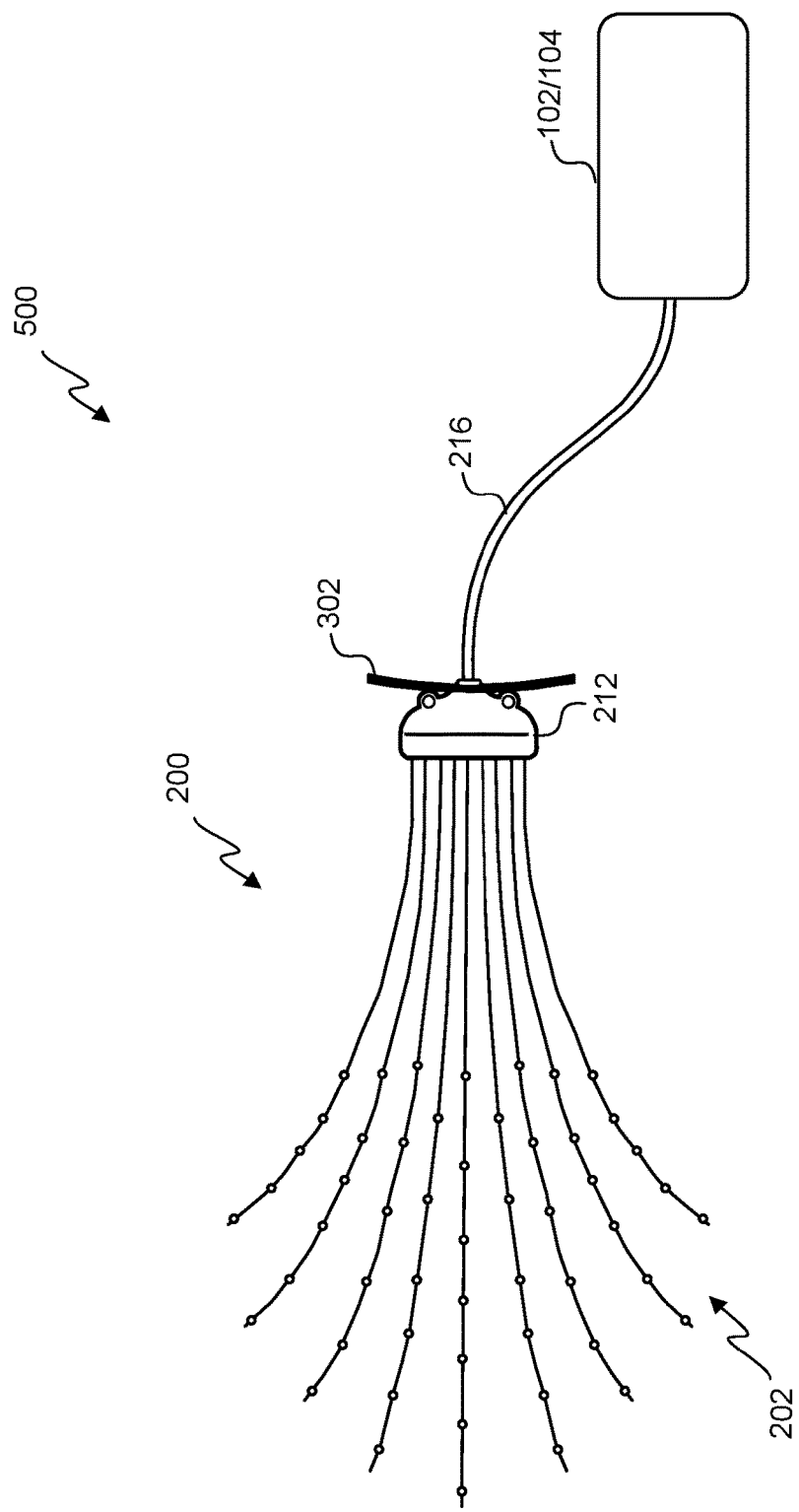
FIG. 5 is a schematic illustration of one embodiment of a pulse delivery system.

With reference now to FIG. 5, a schematic illustration of one embodiment of a pulse delivery system 500 is shown. The pulse delivery system 500 can include the implanted multi-branch stimulation electrode 200 including, for example, branches 202 in the second, implanted position and hub 212. In some embodiments, and as shown in FIG. 5, the lead 216 of the multi-branch stimulation electrode 200 can be connected to the pulse generator 102, 104. In some embodiments, the hub 212 and the branches 202 of the multi-branch stimulation electrode 200 can be implanted within the patient's body, inserted past the incision 302, and the lead 216 can extend through the incision 302 from inside the patient's body to outside the patient's body. The lead 216 and can connect to the pulse generator 102, 104 at a point outside the patient's body. However, in other embodiments, the lead 216 can be entirely implanted within the patient's body and the pulse generator 102, 104 can likewise be entirely implanted within the patient's body.

Figure 6:
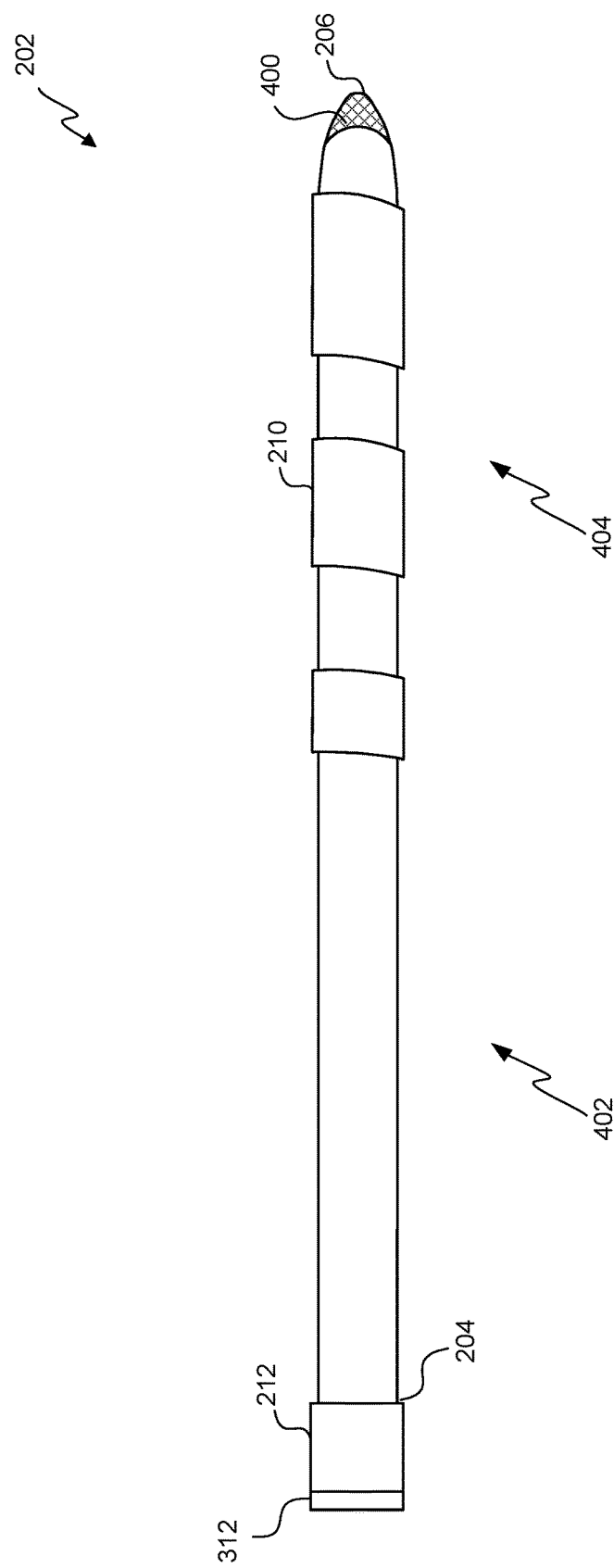
FIG. 6 is a side view of one embodiment of a branch of a multi-branch stimulation electrode.

With reference now to FIG. 6, a side view of one embodiment of one of the branches 202 is shown. The branch 202 can include the proximal end 204 connecting to the hub 212 that contacts the stiffening member hub 312, and the distal end 206. As depicted in FIG. 6, the distal end 206 of the branch 202 can include the insertion member 400. The insertion of the 400 can comprise a variety of shapes and sizes and can be made from a variety of materials. In some embodiments, the insertion member 400 can be configured to interact with the stiffening member 308 during the implantation of the hub 212 to prevent the stiffening member 308 from penetrating through the branch 202. In such embodiments, the insertion member 400 can comprise a penetration material that can be, for example, metal, hard plastic, a composite, and/or any other material capable of interacting with the stiffening member 308 during the implantation and not allowing the stiffening member to penetrate the branch 202. In some embodiments, the insertion member 400 can be further configured to facilitate implantation. In such embodiments, the insertion member 400 can be shaped to facilitate the insertion and can include, for example, a pointed tip.

The branch 202 depicted in FIG. 6 further includes an elastic zone 402 and an inelastic zone 404. The elastic zone 402 can be a portion of the branch 202 that has elastic properties and therefore allows a dimension of the branch 202 to temporarily change in response to the application of a force. In some embodiments, the elastic zone 402 can be located at any position on and/or along the insertion member 202 and the elastic zone 402 can have any desired size and shape.

In some embodiments, the entire branch 202 can be the elastic zone 402, and in some embodiments, the branch 202 can include an inelastic zone 404. The inelastic zone can be a portion of the branch 202 that is not intended to have elastic properties and/or that does not have elastic properties at the load levels applied during the implantation of the multi-branch stimulation electrode 200. In some embodiments, the elastic zone 402 can be located proximate to the proximal end 204 of the branch 202 and the inelastic zone 404 can be located proximate to the distal end 206 of the branch 202. In some embodiments, and as depicted in FIG. 6, the stimulation contacts 210 can be located in the inelastic zone 404. Advantageously, placement of the stimulation contacts 210 in the inelastic zone can decrease stresses created in one or both of the stimulation contacts 210 and the branch 202 during the implantation of the multi-branch stimulation electrode 200 by eliminating and/or decreasing discrepancies between the material properties of the stimulation contacts 210 and the branch 202.

Figure 7A:
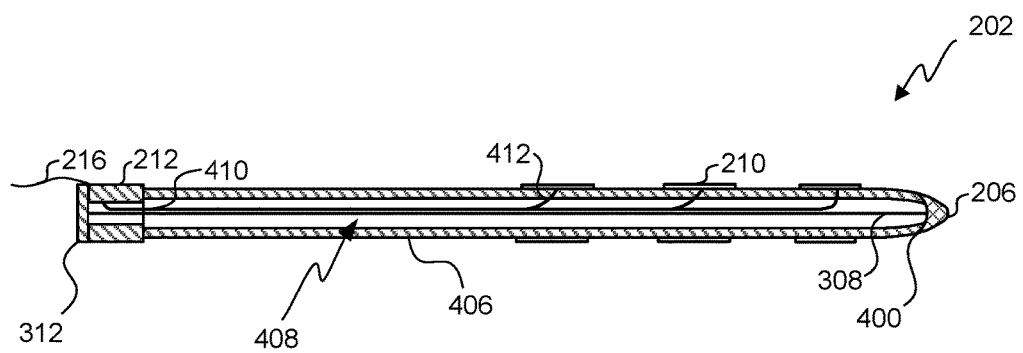
FIGS. 7A-7C are section views of embodiment of branches of a multi-branch stimulation electrode.
Figure 7B:
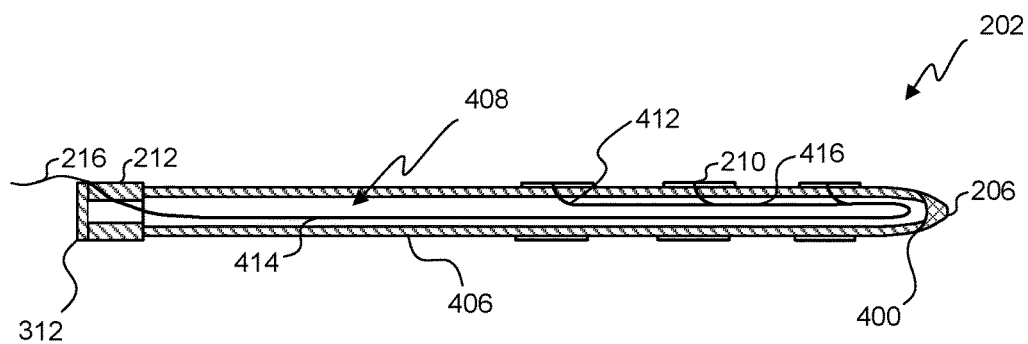
Figure 7C:
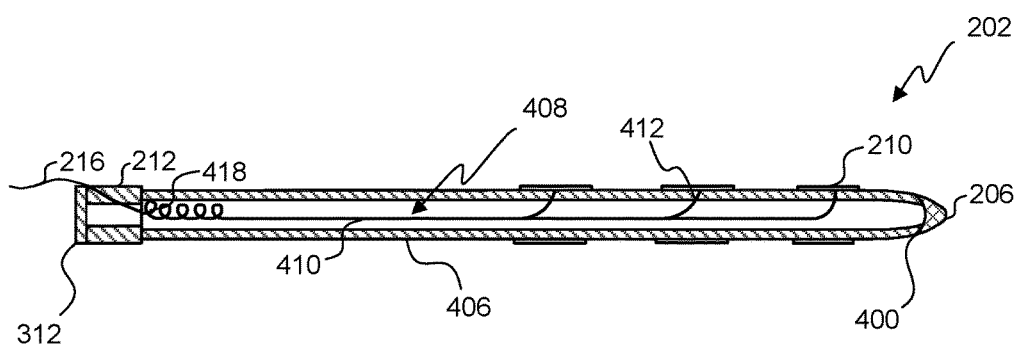

With reference now to FIG. 7A-7C, section views of some embodiments of the branch 202 are shown. With reference now to FIG. 7A, section view of one embodiment of branch 202 is shown. The branch 202 is connected at its proximal end 204 to hub 212, which hub is connected to lead 216 and contacts stiffening element hub 312. The branch 202 further includes a penetrating element 400 located at the distal end 200. In some embodiments, the branch 202 can include one or several branch walls 406 that can define an internal channel 408 of the branch 202. In some embodiments, the internal channel 408 can comprise a single channel that can be, for example, configured to receive a stiffening element 308, and in some embodiments, the internal channel 408 can comprise a channel configured to receive the stiffening element 308 and a channel configured to receive one or several conductors configured to connect the stimulation contacts 210 to the lead 216.

In some embodiments, the one or several conductors can be incorporated into the branch walls 406 of the branch 202, and in some embodiments, the one or several conductors can be loosely contained within the internal channel 408. In the embodiment depicted in FIG. 7A, the branch 202 includes a single internal channel 408 configured to receive both the stiffening element 308, a main wire 410, and a plurality of branch wires 412. In some embodiments, the main wire 410 can carry electrical pulses from the lead 216 to the stimulation contacts 210. In some embodiments, the main wire can connect to the lead 216 in the hub 212 and can be electrically connected to the stimulation contacts 210 via one or several branch wires 412. In some embodiments, the branch wires can include one or several electrical components configured to carry electrical property of the circuit with which the stimulation contact 210 connected to the branch wire 412 is associated. In some embodiments, these electrical components can include one or several resistors, capacitors, or the like.

As further seen in FIG. 7A, in some embodiments, the stiffening element 308 can extend from the stiffening element hub 312 to contact the insertion tip 400. In some embodiments, as slight differences in the length of one or several of the branches 202 and/or of the stiffening elements 308 may arise, the stiffening elements 308 may not adequately stiffen one or several of the branches 202 to allow implantation of the branches 202.

In one embodiment, for example, one of the stiffening elements 308 may be relatively longer than others of the stiffening elements 308 with respect to one or several branches. As such, the relatively longer of the stiffening elements 308 may contact the insertion tip 408 of one of the branches 202 and others of the stiffening elements 308 may not contact the insertion tip 408 of the others of the branches 202.

In some embodiments, the multi-branch stimulation electrode 200 can include one or several features to overcome these problems to thereby facilitate implantation of multi-branch stimulation electrode 200. In some embodiments, these features can include one or several elastic portions of the branches 202. In some embodiments, these features can include one or several features located in the stiffening element 308 and/or in the stiffening element hub 312 that can allow a change to the length of the stiffening element and/or similar features in the hub 212 which can allow changes in the length of the branches 202. Advantageously, such features can allow for improved implantation of the multi-branch stimulation electrode 200.

With reference now to FIG. 7B, a section view of one embodiment of a branch 202 is shown. In this embodiment, the branch 202 includes features configured to facilitate in creating the same and/or similar electrical properties at circuits arising when the branches 202 of the multi-branch stimulation electrode 200 are not parallel spaced, and features configured to allow the branch 202 to stretch so as to compensate for discrepancies in the length of some or all of the branches 202 and/or the stiffening elements 308. As specifically seen, in the embodiment depicted in FIG. 7B, the branch 202 includes extending wire 414 and returning wire 416. The extending wire extends from the hub 212 towards the distal end 206 of the branch 202 wherein the direction of the extension of the wire changes and the returning wire 414 returns towards the hub 212. In some embodiments, this can reverse the order with which the stimulation contacts 210 are connected to the wire which can thereby result in the greatest amount of resistance being experienced at the stimulation contact 210 relatively closest to the hub 212. In some embodiments, this looping of the wire can further provide access wire within the branch 202 such that the wire does not break or stretch if the branch 202 elastically deforms during implantation of the multi-branch stimulation electrode 200.

With reference now to FIG. 7C, a section view of one embodiment of the branch 202 is shown. In this embodiment, the branch 202 includes features configured to allow the branch 202 to stretch so as to compensate for discrepancies in the length of some or all of the branches 202 and/or the stiffening elements 308. As specifically seen, the main wire 410 includes a plurality of extension coils 418 located in the internal channel 408 of the branch 202. In some embodiments, these extension coils 418 can allow the overall length of the main wire 410 to change with changes in the length of the branch 202. Advantageously, this can allow for the elastic deformation of the branch 202 without stretching and/or breaking the main wire 410. The extension coils can comprise a variety of shapes and sizes and can include, for example, any desired number of loops or coils. In some embodiments, the extension coils 418 can be designed according to expected changes in the length of the branch 202.

In the foregoing specification, the invention is described with reference to specific embodiments thereof, but those skilled in the art will recognize that the invention is not limited thereto. Various features and aspects of the above-described invention can be used individually or jointly. Further, the invention can be utilized in any number of environments and applications beyond those described herein without departing from the broader spirit and scope of the specification. The specification and drawings are, accordingly, to be regarded as illustrative rather than restrictive. It will be recognized that the terms "comprising," "including," and "having," as used herein, are specifically intended to be read as open-ended terms of art.

What is claimed is:

1. An implantable electrode array system, comprising:
   (a) a multi-branch electrode array, the multi-branch electrode array comprising a plurality of elongated branches extending along an insertion axis, wherein each branch includes at least one electrode contact and a blunt dissecting distal tip;
   (b) a plurality of removable stiffening components configured to bias the plurality of elongate branches toward a deployed configuration, wherein the plurality of stiffening components are linked by a stiffening element hub, wherein each of the plurality of stiffening components extends through at least a portion of one of the plurality of elongated branches; and
   (c) an implantation cartridge for moving the multi-branch electrode array from a retracted position to a deployed position, wherein the branches are maintained in a retracted configuration when the multi-branch electrode array is in the retracted position, wherein, when in the retracted position, the branches are positioned proximally relative to the implantation cartridge, and, wherein, when in the deployed position, the branches are in the deployed configuration and extend distally and laterally outwardly along a first transverse orientation, relative to the insertion axis, from the implantation cartridge a further distance than in the retracted configuration;
   wherein, when in the deployed configuration, the branches are positioned with a first branch disposed between a second branch and a third branch, and a fourth branch disposed between the second branch and the first branch so that the electrode array is distributed along a thin surface.

2. The implantable electrode array system of claim 1, wherein the stiffening components are configured to increase the stiffness of the branches to facilitate blunt dissecting by the branches.

3. The implantable electrode array system of claim 2, wherein at least some of the branches are configured to receive the stiffening elements.

4. An implantable electrode array system, comprising:
   (a) a multi-branch electrode array, the multi-branch electrode array comprising a plurality of elongated branches extending along an insertion axis, wherein each branch includes at least one electrode contact and a blunt dissecting distal tip; and
   (b) an implantation cartridge for deploying the multi-branch electrode array from a retracted configuration to a deployed configuration, wherein, when in the retracted configuration, the branches are positioned proximally relative to the implantation cartridge, and, wherein, when in the deployed configuration, the branches extend distally and laterally outwardly along a first transverse orientation, relative to the insertion axis, from the implantation cartridge a further distance than in the retracted configuration; and
   wherein, when in the deployed configuration, the branches are positioned with a first branch disposed between a second branch and a third branch, and a fourth branch disposed between the second branch and the first branch so that the electrode array is distributed along a thin surface, wherein at least some of the branches include stiffening components configured to increase the stiffness of the branches to facilitate blunt dissecting by the branches, and wherein the stiffening component comprises a biodegradable outer layer on at least some of the branches.

5. The implantable electrode array system of claim 1, wherein the multi-branch electrode array further comprises a hub comprising anchor features configured to be anchored to a tissue.

6. The implantable electrode array system of claim 1, wherein the stiffening components are simultaneously displaceable by displacement of the stiffening element hub.

7. The implantable electrode array system of claim 1, wherein the implantation cartridge comprises an elongate member having a U-shaped cross-section.

8. The implantable electrode array system of claim 7, wherein the implantation cartridge comprises an insertion sleigh displaceably retained within the elongate member.

9. The implantable electrode array system of claim 8, wherein the multi-branch electrode array is detachably coupled to the insertion sleigh.

10. The implantable electrode array system of claim 1, further comprising an implantable neurostimulation pulse generator configured to generate one or more neurostimulation electrical signals.

11. The implantable electrode array system of claim 1, wherein at least some of the electrode contacts are configured as anode electrode contacts and wherein at least some of the electrode contacts are configured as cathode electrode contacts.

12. The implantable electrode array system of claim 1, wherein all of the electrodes on one branch are configured as anode electrode contacts and wherein all of the electrodes on an adjacent branch are configured as cathode electrode contacts.

13. The implantable electrode array system of claim 1, wherein a size of the electrode contacts varies as a function of position on at least some of the branches.

* * * * *